United States Patent [19]

diZerega

[11] Patent Number: 5,015,629

[45] Date of Patent: May 14, 1991

[54] TISSUE REPAIR

[75] Inventor: Gere S. diZerega, Pasadena, Calif.

[73] Assignee: University of Southern California, Los Angeles, Calif.

[21] Appl. No.: 494,914

[22] Filed: Mar. 9, 1990

Related U.S. Application Data

[63] Continuation of Ser. No. 372,209, Jun. 26, 1989, abandoned, Continuation of Ser. No. 50,581, May 12, 1987, abandoned.

[51] Int. Cl.$^5$ .................... A61K 37/02; C07K 7/14
[52] U.S. Cl. ..................................... 514/16; 530/316
[58] Field of Search ........................ 514/16; 530/316

[56] References Cited

PUBLICATIONS

Eisai Co., Ltd., Chem. Abstracts, vol. 104:10586a (1986).
David M. Form and Robert Auerbach, "PGE$_2$ and Angiogenesis" (41548), Proceedings of the Society for Experimental Biology and Medicine (1983) 172, 214–218.
Abstracts of Papers, Federation of American Societies for Experimental Biology, 71st Annual Meeting, Washington, D.C., Mar. 29–Apr. 2, 1987, Papers: No. 2750 Tumor Necrosis Factor Induces Neovascularization and Sustained Vascular Permeability in the Rabbit Eye, James T. Rosenbaum et al., p. 788.
No. 3242 Prostaglandins and Corneal Neovascularization, E. Y. Tong et al., p. 872.
No. 5146 Interleukin-1 Induces Corneal Neovascularization, R. A. Prendergast et al., p. 1200.
Montz et al., Postsurgical Mesothelial Reepithelialization, p. 31, *Reproductive Surgery*, DeCherny and Plan (Eds.), Year Book Medical Publ., Chicago, 1985.
Hunt et al., Coagulation and Macrophage Stimulation of Angiogenesis and Wound Healing, Denee, P. (Ed.), p. 1, *Surgical Wound*, Philadelpha (1982).
Auerbach, R., Angiogenesis-Inducing Factors, Lymphokines 4:69, 1981.
Folkman, J., Angiogenesis: Initiation and Control, Ann. N.Y. Acad. Sci., 401:212, 1982.
Gullino, P. M., Angiogenic Factors: A Review, Handbook Exp. Pharm. 57:427, 1981.
Folkman, J., Klagsbrun, M., Angiogenic Factors, Science 235:422, 1987.

Howard, B. V. et al., Characterization of the Collagen Synthesized by Endothelial Cells in Culture, Proc. Nat'l. Acad. Sci., U.S.A., 73:2361–2364, 1976.
McGrath, M. H., Emery III, J. M., The Effect of Inhibition of Angiogenesis in Granulation Tissue on Wound Healing and the Fibroblast, Annals Plastic Surg. 15:105, 1985.
Gospodarowicz, D. et al., Clonal Growth of Bovine Vascular Endothelial Cells: Fibroblast Growth Factor as a Survival Agent, Proc. Nat'l Acad. Sci., U.S.A., 73: 4120–4124, 1976.
Gospodarowicz, D. et al., The Angiogenic Activity of the Fibroblast and Epidermal Growth Factor, Exp. Eye Res. 28: 501–504, 1979.
Grotendorst, G. R. et al., Molecular Mediators of Tissue Repair, p. 201, *Soft and Hard Tissue Repair*, T. K. Hunt et al. (Eds.), Praege, N.Y., 1984.
Langman, J., Medical Embryology, Baltimore, Md., Williams & Wilkins Co., 1969.
Hudlicka, O., Tyler, K. R., Angiogenesis: The Growth of the Vascular System, Academic Press, London, Harcourt, Brace, Jovanovich, 1986.
Silver, I. A., Cellular Microenvironment in Healing and Non-Healing Wound, p. 50, *Soft and Hard Tissue Repair*, T. K. Hunt et al. (Eds.), Praege, N.Y., 1984.
Jane L. Frederick et al., "Initiation of Angiogenesis by Human Follicular fluid", Science, vol. 224, pp. 389–390 (27 Apr. 1984), Abstract.
The Merck Index, 10th Ed., 1983, p. 678.
Leonardo A. Fernandez et al., "Neovascularization Produced by Angiotensin II", *J. Lab. Clin. Med.* (1985), 105, 141–145.
Judah Folkman and Michael Klagsbrun, "Angiogenic Factors", *Science* (1987), 235, 442–447.
J. K. Findlay, "Anhgiogenesis in Reproductive Tissues", *J. Endocr.* (1986), 11, 357–366.
Robert D. Koos, "Stimulation of Endothelial Cell Proliferation by Rat Granulosa Cell-Conditioned Medium", *Endocrinology* (1986), 119, No. 2, 481–488.
Abstract, "Angiogenesis Induced by Degradation Products of Hyaluronic Acid", *Science* (1985), 228, 1324–1326.

*Primary Examiner*—Jacqueline Stone
*Attorney, Agent, or Firm*—Nillson, Robbins, Dalgarn, Berliner, Carson & Wurst

[57] ABSTRACT

A method for increasing the rate of healing in mammalian tissue includes the administration of a solution of angiotensin II.

5 Claims, 1 Drawing Sheet

TISSUE REPAIR

This is a continuation of co-pending application Ser. No. 07/372,209 filed on June 26, 1989, which is a continuation of co-pending application Ser. No. 07/050,581 filed on May 12, 1987, both now abandoned.

FIELD OF THE INVENTION

This invention relates generally to the fields of biochemistry and medicine, and more specifically to methods and substances for accelerating the growth or healing of tissue.

BACKGROUND AND SUMMARY OF THE INVENTION

A wound (i.e., a laceration or opening) in mammalian tissue results in tissue disruption and coagulation of the microvasculature at the wound face, and repair of such tissue represents an orderly, controlled cellular response to injury.

Tissue growth and repair are biologic systems where cellular proliferation and angiogenesis occur in the presence of an oxygen gradient. Wound healing represents an orderly, controlled cellular response to injury. The sequential morphologic and structural changes which occur during tissue repair have been characterized in great detail and have in some instances been quantified. Raftery, A. T., "Regeneration of Parietal and Visceral Peritoneum", *Brit. J. Surg.*, Vol. 60, p. 293 (1973). All soft tissue wounds, regardless of size, heal in a similar manner. Injury results in tissue disruption and coagulation of the microvasculature at the edge of the wound. The cellular morphology consists of three distinct zones. The central avascular wound space is oxygen-deficient, acidotic, hypercarbic, and has high lactate levels. Adjacent to the wound space is a gradient zone of local anemia (ischemia) which is populated by dividing fibroblasts. Behind the leading zone is an area of active collagen synthesis characterized by mature fibroblasts and numerous newly-formed capillaries (i.e., neovascularization). While this new blood vessel growth (angiogenesis) is necessary for the healing of wound tissue, angiogenic agents have heretofore been unable to fulfill the long-felt need of providing the additional biosynthetic effects of tissue repair.

Despite the need for more rapid healing of wounds, i.e., severe burns, surgical incisions, lacerations and other trauma, there is presently no practical way to accelerate wound healing with pharmacological agents.

The invention comprises a method for increasing the rate of healing of wound tissue, comprising the application to such tissue of angiotensin II in an amount which is sufficient for said increase. As explained in the detailed description which follows, it has been found that the application of angiotensin II to wound tissue significantly increases the rate of wound healing, leading to a more rapid re-epithelialization and tissue repair.

The term angiotensin II refers to the octapeptide present in humans and other species, and has the sequence Asp-Arg-Val-Tyr-Ile-His-Pro-Phe. Angiotensin II is a known pressor agent and is commercially available.

DETAILED DESCRIPTION OF THE PREFERRED EMBODIMENT

Figure 1:
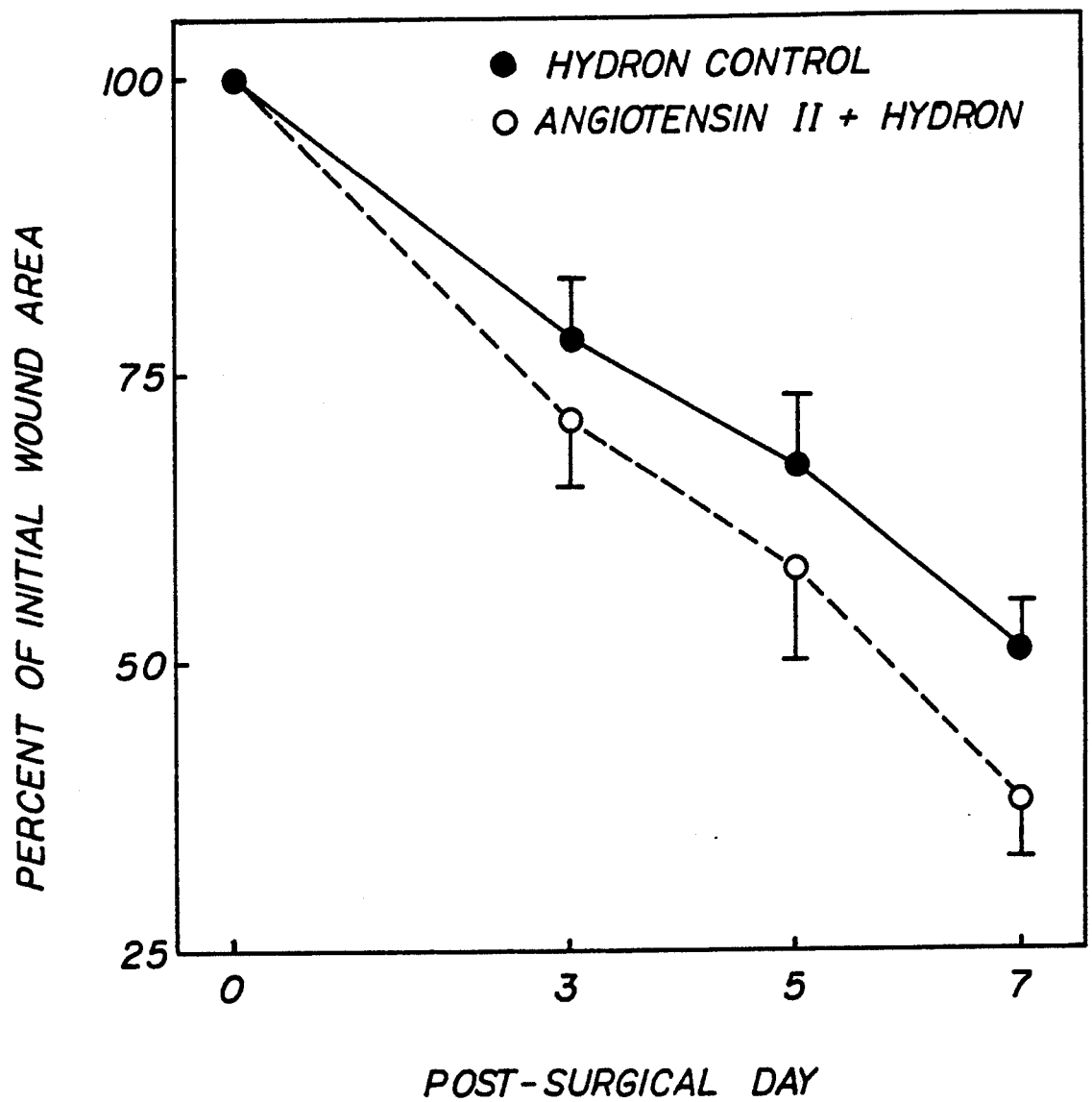

The biological formation of angiotensin is initiated by the action of renin on the plasma substrate angiotensinogen. The substance so formed is a decapeptide called angiotensin I which is converted to angiotensin II by the converting enzyme angiotensinase which removes the C-terminal His-Leu residues from angiotensin I.

Angiotensin II is one of the most potent vasoconstrictors known, causing constriction of the small arteries that branch to form the capillaries, i.e., the arterioles.

According to the method of the invention, angiotensin II is applied to wound tissue in amounts sufficient to increase the healing rate of tissue. It has been found that this octapeptide can significantly accelerate the rate of healing at nanogram levels both in vitro and in vivo. Specifically, the rate of neovascularization in wound tissue is increased when a solution containing as low as 5 nanograms per milliliter of angiotensin II is applied to the tissue, and a significant increase in capillary proliferation is provided when a solution containing at least 5 micrograms per milliliter is employed. Specific examples described herein show significant angiogenic action with solutions containing from 1 to 600 micrograms per milliliter of angiotensin II.

The octapeptide may be applied in a variety of solutions, which are sterile, which dissolve sufficient amounts of the protein, and which are not harmful to wound tissue. In this regard, angiotensin II is very stable but is hydrolized by strong acids and bases. The octapeptide is soluble in organic solvents and in aqueous solutions at pH 5-8.

Any type of application means may be employed which permits the influx of angiotensin II into the tissue over a period of time. For example, an aqueous solution of angiotensin II could be applied to the wound tissue through a gauze bandage or strip, or such a solution could be formulated so that a timed perfusion may be obtained, e.g., liposomes, ointments, micells, etc. Methods for the production of these formulations with angiotensin II will be apparent to those of ordinary skill in the art. The particular concentration of angiotensin II which is employed is not critical since the tissue-repairing effect is present even when the octapeptide is present in nanogram quantities.

Preferably, a matrical or micellar solution is employed with the angiotensin II present in a concentration of at least 5 micrograms per milliliter. A particular matrical solution which has been used to advantage in the described examples is a semi-solid polyethylene glycol polymer sold under the trademark Hydron by the Hydro Med Sciences. Another preferred solution is a micellar solution sold under the trade name Pluronics F108 by the BASF company. Under room temperature conditions, this solution is a liquid, but when applied to warm tissue the solution forms a gel which permits the infusion of angiotensin II into the wound tissue for a period of several days.

The healing effects of angiotensin II may be provided in a variety of instances. The solution may be applied topically to surface wound tissue in the treatment of severe burns, trauma, stasis ulcers, lacerations and other conditions. In addition, interperitoneal wound tissue such as that resulting from invasive surgery may be treated with angiotensin II solutions to accelerate healing. For example, following the surgical removal of a colon section or other tissue, the surgical plane may be coated with angiotensin II solution prior to closing the surgical site in order to accelerate internal capillary perfusion and healing. In addition, the rate of localized healing may be increased by the subdermal administration of angiotensin II by injection or otherwise.

EXAMPLES

Wound Healing

In order to document the effect of angiotensin II, several models were chosen. In a first example, the healing of an occluded full-thickness excision was studied. Adult male rats were anesthetized, and four square centimeter excisions extending through the panniculus carnosus were made mid-dorsally on five or six animals per treatment group. Immediately after this wounding, all excisions were covered with dressings backed with telfa tape. These dressings were held in place with an elastic bandage.

Each wound was treated daily for eight days after wounding by lifting the dressing and injecting 0.2 ml of a solution of five micrograms per milliliter human angiotensin II in Hydron by subdermal administration. Other rats were injected with a five micrograms per milliliter solution of angiotensin II in sterile physiological saline solution by use of a microsyringe. Control excisions were treated with pure Hydron or physiological saline.

This method for evaluating the effect of angiotensin II on wound healing was chosen because wound contraction permits measurement of repair. In addition, granulation tissue is present in quantities allowing biochemical evaluation if desired. The repair process is at its most dynamic level during this time interval, and is most sensitive to positive or negative influences. This full-thickness incision is currently recommended by the United States Food and Drug Administration for testing adverse repair effects of wound antiseptic agents.

The excisions were occluded in order to optimize repair, while ensuring that the injected agent was not prevented from reaching the wound by any hard tissue which forms on air-exposed wounds. Repair was quantified as percent excision contraction during the eight days of treatment. Wound areas were measured at the time of wounding and daily thereafter and percent contraction was calculated for each wound as day zero area minus day eight area divided by the day of measurement area. Delay of repair was calculated as the reduction below the average percent contraction of an occluded untreated control group. The surface area of the wound was measured at two-day intervals by tracing the perimeter of the wound onto flexible paper. The areas of irregular figures were calculated by trapezoidal integration.

Control excisions contracted an average of 50% during the first eight days after wounding, with individual means ranging from 40-60%. Daily treatment with 0.2 ml sterile physiological saline, distilled water or Hydron did not alter the contraction rate. Compared with these control wounds, the granulation tissue in the wounds treated with angiotensin II appeared redder, spongier, more friable and bled more heavily when incised for tissue sampling.

Plotting the open wound areas over time produced a wound healing curve for each experimental group. This curve is shown in FIG. 1. An initial enlargement of the wound resulting from elasticity of the surrounding skin was followed by a lag phase, and then a rapid decrease in the size of the wounds. Inspection of the curves shows that the control group is significantly different from the treatment group. A non-linear regression coefficient was determined for each healing curve for each animal and, using this parameter for each animal, one-way analysis of variance showed significant differences among the groups. Before the seventh day after wounding, when epithelial ingrowth at the wound margins was first visible in all of the wounds, the healing curve describes the process of wound contraction. The treated wounds demonstrated a significant increase in wound contraction. The treated wounds started to contract at the same time as the controls, but wound healing of the treated wounds increased substantially with time. In addition, granulation tissue was viewed by light microscopy and the tissue from the treated wounds were different from the control tissue. Although the number of fibroblasts and inflammatory cells was similar, the pattern of vessel orientation perpendicular to the wound surface as well as the number of new vessels was markedly increased in the treated rats as compared to the controls.

In Vitro Studies

In a second example, the effects of angiotensin II on proliferation (mitogenesis) and directional migration (chemotaxis) of endothelial cells were determined. In this regard, it is important to consider that tissue repair requires proper neovascularization, and that new blood vessel growth for wound repair requires endothelial cell replication, migration and orientation. Wound healing factors must be able to stimulate chemotaxis and cell proliferation in addition to initiating new blood vessel growth. The proliferation (mitogenesis) and the directional orientation of such cells (chemotaxis) was studied in vitro using bovine aortal endothelial cells.

Mitogenesis

In the study of mitogenesis, the bovine aortic endothelial cells were seeded into 96-well microtiter plates in culture medium with 10% fetal bovine serum. After twenty-four hours, the medium was removed from the adherent cells and replaced by culture medium with 1% fetal bovine serum containing zero, 0.3, 1.0, 3.0 and 10.0 nanograms/ml human angiotensin II. After a two-day incubation, the cells were pulsed for six hours with 3H-thymidine, washed, incubated with 0.1% trypsin, and harvested onto filter paper with an automatic cell harvester. The cell harvester washed the trypsinized cells from each culture well with phosphate-buffered saline, followed by a wash of the cells trapped on the filter paper with 10% trichloroacetic acid. The area on the filter paper associated with each well of the microtiter plate was then removed and placed in a plastic scintillation vial. The filter paper was incubated at room temperature overnight with 0.25N NaOH, and a scintillation cocktail was then added. The amount of trichloroacetic acid precipitable radioactivity for each culture well was then determined with a scintillation counter. The results are reported as a stimulatory ratio, where the ratio of radioactivity counts from the treated group divided by the counts from the untreated group, and are seen in Table 1. Due to the cellular requirement for the culture medium, the highest concentration of angiotensin II used in the mitogenesis assay was a 1:10 dilution. As is seen in the Table, angiotensin II induced at least a 1½-fold increase in the proliferation of endothelial cells at concentrations of from three to ten ng/ml.

Chemotaxis

To determine the effect of angiotensin II on the directional orientation of cells, bovine endothelial cells were labelled for eighteen hours with 3H-thymidine, washed and seeded into blind well chambers with ten ng/ml solutions of angiotensin II in the lower chamber. The cells were allowed to migrate towards the angiotensin II across polyvinylpyrrolidone-coated polycarbonate membranes with 8 μm pores for two hours. The membranes were removed from the chambers, and the cells were scraped from the loading (top) side. The remaining cells (those that migrated to the under side of the membrane) were then dissolved on the filter with 0.25N NaOH. Background radioactivity (noncell-associated) was assessed by removing some filters immediately after the addition of cells prior to cellular migration, and processing these control filters the same way as the test filters. Cellular migration is reported either as a stimulatory ratio, as defined above with respect to mitogenesis, or as the actual number of cells migrating to the lower side of the filter. The latter was calculated by the following formula:

$$\text{No. of Cells} = \frac{(R - B)}{(T - S)/(V)(C)}$$

where R equals the radioactivity in cpm associated with each test filter, B equals the cpm obtained from the background filters, T equals the cpm obtained from a volume (V) of cells in suspension at a known concentration (C) and S equals the cpm obtained from the cell supernate (noncellular, or unbound radioactivity).

Angiotensin II was added on the same side of the membrane as the cells, the opposite side, or both. When a positive gradient of angiotensin II was present, that is, a higher concentration of angiotensin II existed on the side of the membrane opposite the cells, the cells exhibited directional migration toward the higher concentration even though the osmotic pressure of the solutions was the same. More migration occurred when the cells were exposed to angiotensin II in equal concentrations above and below the membrane (equal gradients) than when angiotensin II was not added. However, none of the equal gradients resulted in cell migration that exceeded that seen with the positive gradients. Inverted gradients (i.e., a higher concentration of angiotensin II above the filter than below) resulted in fewer cells on the under side of the filter than were seen with the equal gradients. This was presumably due to the effects of chemotaxis, in a reverse direction, overcoming those of chemokinesis. Angiotensin II was chemotactic at dilutions of from 0.3–10 ng/ml with an $ED_{50}$ of 3 nanogram/ml.

The effectiveness of angiotensin II in matrical and micellar solutions is demonstrated by the use of these delivery vehicles in the testing of the ability of this compound to provide the angiogenic effect which is necesary for wound healing. Angiotensin II was mixed with an equal volume of a polyethylene glycol matrical solution containing 10% Hydron, 60% ethanol and 1% polyethylene glycol. The effect of the angiotensin II-Hydron mixture on angiogenesis was assessed in New Zealand White female rabbits. The rabbits were anesthetized and a 20 μl aliquot of the angiotensin II-hydron solution was injected into the right cornea by aseptically creating a pocket 1 mm proximal to the superior limbus. The left cornea of each animal was injected with hydron and saline as a control. The corneas were evaluated daily for fifteen days after implantation, and sustained growth of well-defined new capillaries from the limbus toward or into the corneal implant was considered positive for angiogenesis. The angiotensin II solution stimulated angiogenesis in all rabbits. The invasion of blood vessels was macroscopically visible by the third post-injection day and extended 3 mm into the site of the injection from the closest region of the cornealscleral limbus by day nine. All rabbits treated with the Hydron-angiotensin II solution demonstrated intracorneal vessels greater than 1 mm from limbus toward injection site by ten days after the injection.

A detailed illustrative embodiment of the invention has thus been described in the manner required to enable the use of angiotensin II in the promotion of healing in mammalian tissue. However, it is to be understood that the embodiments set forth merely exemplify the invention, which may take forms that are different from the illustrations disclosed. For example, angiotensin II may be administered to tissue in a wide variety of forms. Therefore, specific details are not to be interpreted as limiting, but rather as forming a basis for the claims which define the scope of this invention.

TABLE 1
MITOTIC ACTIVITY OF ENDOTHELIAL CELLS IN RESPONSE TO VARYING DOSES OF AF (CPM/$10^4$ CELLS) $^3$H THYMIDINE INCORPORATION

|   | 0 hr | 24 hr | 48 hr |
|---|---|---|---|
| 0 | 160 | 185 | 142 |
| .1 | 165 ± 18 | 1,250 ± 116 | 21,842 ± 1,840 |
| .3 | 194 ± 21 | 2,987 ± 211 | 24,628 ± 987 |
| NG OF AF | | | |
| 1 | 135 ± 52 | 5,764 ± 324 | 18,620 ± 1,564 |
| 3 | 115 ± 21 | 15,821 ± 191 | 29,825 ± 2,024 |
| 10 | 185 ± 21 | 19,621 ± 158 | 27,642 ± 2,642 |

I claim:

1. A method for accelerating re-epithelialization of wound tissue in a mammal, comprising applying to said wound tissue an amount of angiotensin II effective for said acceleration.

2. The method of claim 1 wherein the angiotensin II is applied in a solution containing at least five nanograms per milliliter of angiotensin II.

3. The method of claim 2 wherein the solution contains angiotensin II in a concentration of from about one to 600 μg/ml.

4. The method of claims 1, 2 or 3 wherein the angiotensin II is applied in a matrical solution.

5. The method of claim 1, 2 or 3 wherein the angiotensin II is applied in a micellar solution.

* * * * *